United States Patent [19]
Zajac et al.

[11] Patent Number: 5,956,151
[45] Date of Patent: Sep. 21, 1999

[54] BEVERAGE FRESHNESS MONITOR

[76] Inventors: Gerry W. Zajac, 2 So. 624 Marie Curie La., Warrenville, Ill. 60555; James M. Gallas, 1615 Wood Quail, San Antonio, Tex. 78248; Richard Panosh, 101 S. Canyon Dr., Bolingbrook, Ill. 60490

[21] Appl. No.: 09/238,993
[22] Filed: Jan. 28, 1999
[51] Int. Cl.⁶ .......................... G01N 21/00; A23F 31/00
[52] U.S. Cl. .............................................. 356/436; 99/285
[58] Field of Search .................................... 356/338, 409, 356/410, 433, 434, 442, 436, 432; 250/573, 574, 576, 577, 226, 229; 426/231, 432, 433, 595; 99/285

[56] References Cited

U.S. PATENT DOCUMENTS

| | | |
|---|---|---|
| 3,576,646 | 4/1971 | Alwood ..................................... 99/285 |
| 3,606,829 | 9/1971 | Alwood ..................................... 99/285 |
| 3,974,758 | 8/1976 | Stone, Jr. .................................. 99/275 |
| 4,156,031 | 5/1979 | Hamell et al. ........................... 426/541 |
| 4,891,231 | 1/1990 | Mai et al. ................................. 426/52 |
| 4,925,681 | 5/1990 | Mai et al. ................................. 426/52 |
| 5,384,143 | 1/1995 | Koyama et al. ........................ 426/546 |
| 5,714,094 | 2/1998 | Bertholet et al. ....................... 252/403 |
| 5,724,882 | 3/1998 | Gallas et al. .............................. 99/285 |

*Primary Examiner*—Frank G. Font
*Assistant Examiner*—Michael P. Stafira
*Attorney, Agent, or Firm*—Robert L. Marsh

[57] ABSTRACT

Fresh coffee is transmissible to red light, but as the coffee becomes stale, the organic compounds degrade and the brew becomes less transmissible to the light. To monitor coffee freshness, a beam of light is passed through a transparent coffee pot and the transmissibility of the brew is displayed as a measure of freshness.

13 Claims, 4 Drawing Sheets

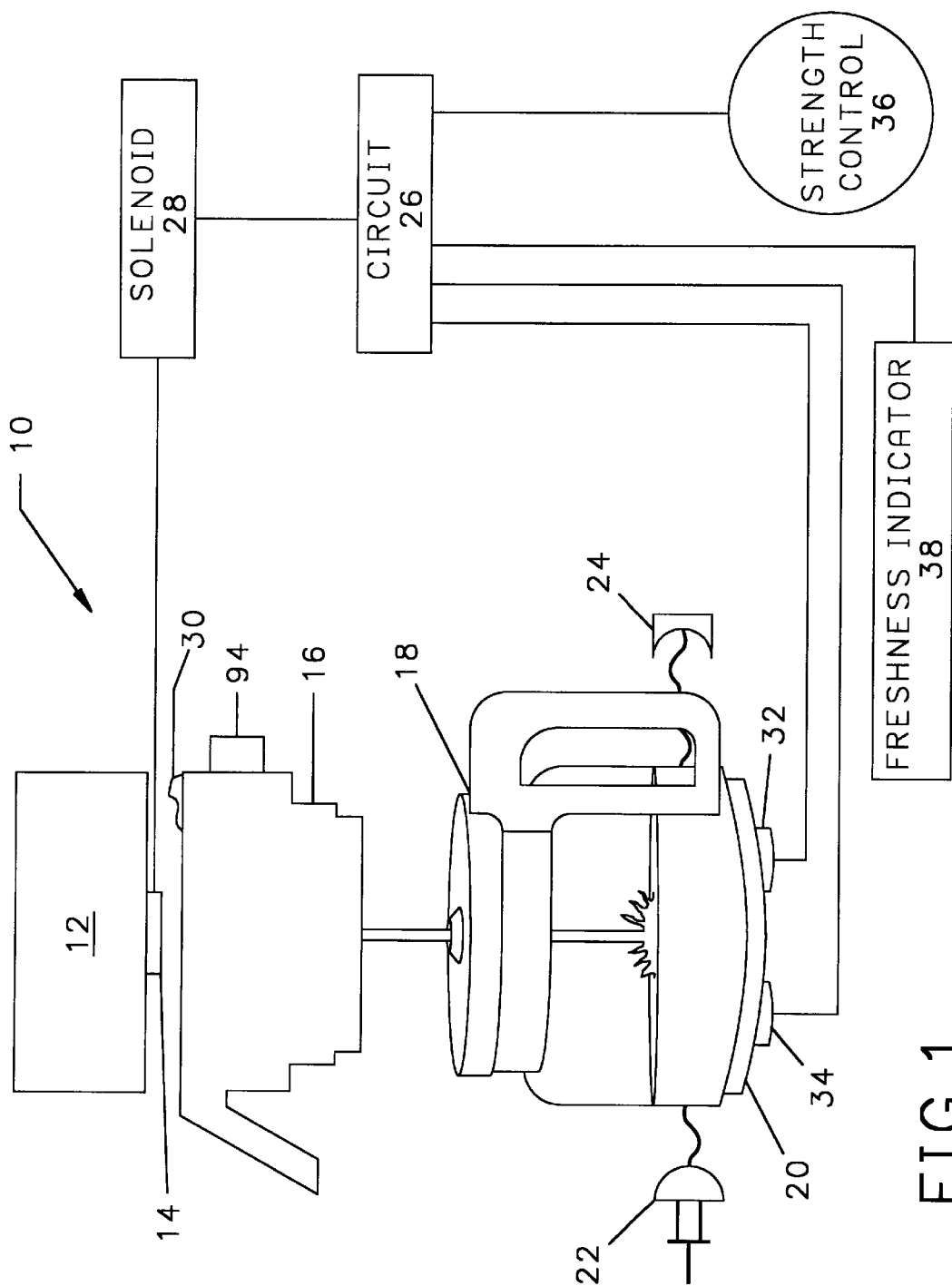

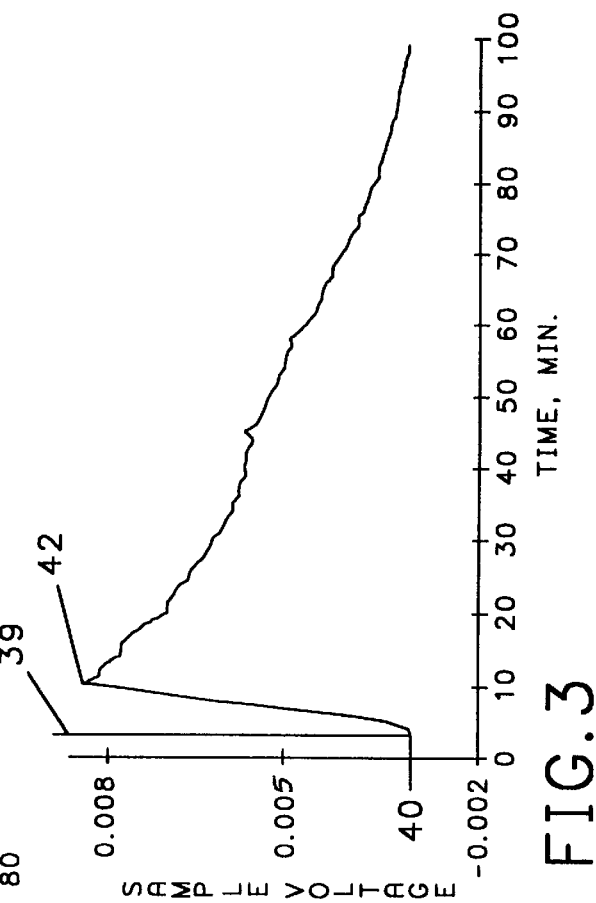
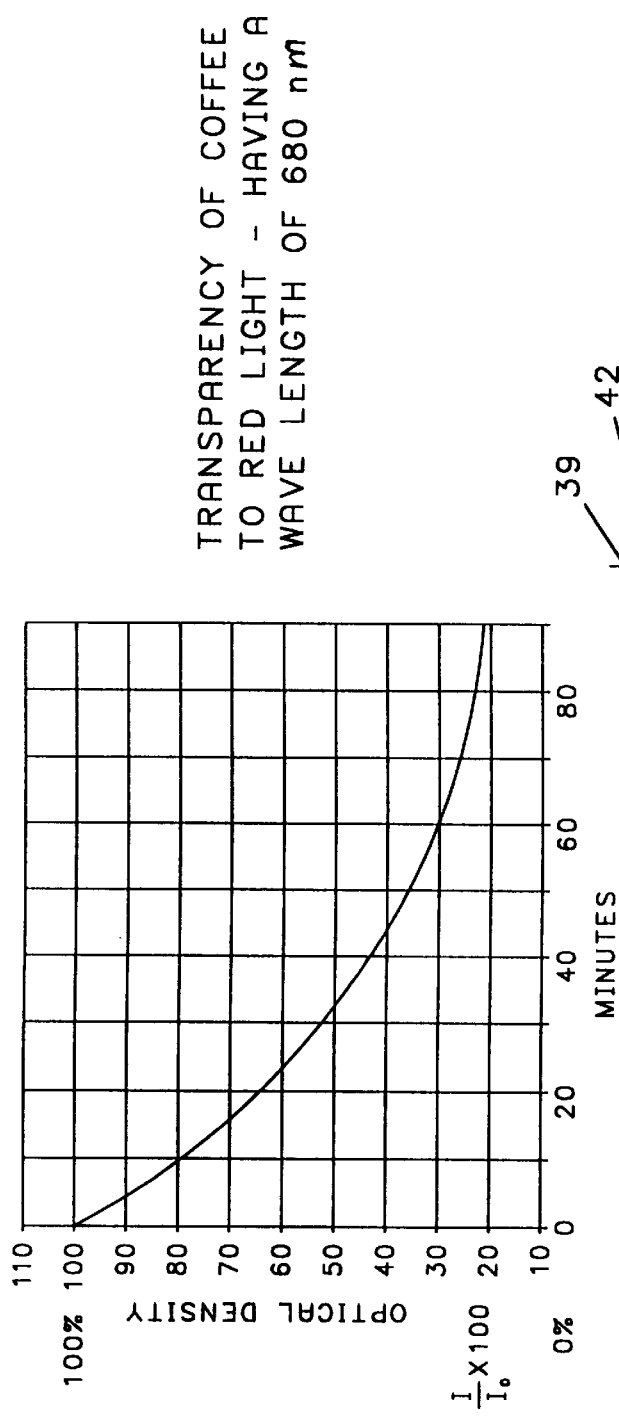

BEVERAGE FRESHNESS MONITOR

The present invention relates to a method and apparatus for monitoring the freshness of fresh brewed coffee and for providing a readout of the freshness on a suitable display.

BACKGROUND OF THE INVENTION

Coffee is a beverage that has a taste and aroma which is more desirable when it is fresh than when it is older and "stale." This is because the compounds which contribute flavor to the coffee are organic in nature and the flavor is the most desirable immediately after the coffee is brewed because the compounds which impart the flavor have not degraded. Over a period of time the organic compounds of the coffee oxidize by combining with oxygen in the water from which the coffee is brewed and the oxidation results in the degradation of the coffee and the loss of the desirable flavor.

There are numerous brands and types of coffees available, and coffee can be brewed such that it is "strong" or "weak" or to any intermediate strength. Individuals who regularly drink coffee desire that the brew have a "strength" and level of "freshness" which is satisfactory to their own palate, and therefore the strength and the freshness of coffee are critical variables to connoisseurs of coffee.

One who makes a pot of coffee may grind or purchase his choices of coffee grinds and place those grinds within the hopper of a coffee maker. Hot water is either percolated through the grinds or it may flow from a reservoir above the hopper through the grinds to a removable coffeepot below the hopper. The degradation of the coffee commences as the pot is filling with coffee and proceeds at a rate that may vary depending on the type of coffee and the degree of the grinding.

In our previous U.S. Pat. No. 5,724,882, we disclosed a coffee maker having an optical feedback system in which a red light from an LED was directed through a transparent coffee pot and the intensity of the light passing through the liquid was monitored to make a brew having a predetermined concentration. U.S. Pat. No. 5,724,882, therefore, disclosed a method and apparatus for brewing coffee to a predetermined strength. Coffee from a coffee maker in accordance with our prior invention will nonetheless become stale over time, and a connoisseur of coffee employing such a coffee maker could not ascertain whether the coffee has become too stale for his palate without tasting it. It would be desirable, therefore, to provide a coffee maker which would brew coffee at a desirable concentration or strength and which would also provide a readout of the freshness of the brew remaining in the pot.

SUMMARY OF THE INVENTION

Briefly, the present invention is embodied in a coffee maker having a hopper for retaining coffee grinds from which coffee would be brewed and having a heating element below the hopper a generally planar upper surface for receiving a coffeepot. The coffee maker further includes a source of hot water, which may be a heated reservoir positioned above the hopper and a control valve for controlling the flow of hot water from the reservoir through the coffee grinds and into the pot on the heating element below.

In accordance with the invention, the pot is transparent and the device further includes a light source or LED for providing a beam of light having wavelengths in the ultra violet, visible, or near infrared range which is directed through the lower portion of the coffee pot to a photodetector on the opposite side of the coffee pot. The device further includes a circuit for measuring the intensity of light detected by the photodetector by measuring the voltage output of the photodetector to determine the transmittance of light through the coffee.

We have found that the organic components which make up fresh coffee are partially transparent to the light waves especially to red light waves from an LED but as the organic matter which imparts flavor to the coffee degrades and the coffee brew becomes progressively more stale, the transparency of the brew to the light also progressively decreases. We have found that the voltage output of the photo detector drops at a rate which corresponds to the rate at which the coffee looses its freshness and becomes stale and therefore a display of the downward progression of the voltages from the photo detectors is also a display of the deterioration of the freshness of the coffee.

In accordance with the invention, the circuitry of the device includes a means for digitally measuring the voltage potential of the LED and storing that voltage in a first register. Subsequent voltage measures are thereafter compared to the first voltage in a first comparator and if the new voltage is larger than the old, replacing the new voltage with the old until a maximum voltage is found. In like manner a second register and a second comparator are used to find a minimum voltage output from the photodetector. The maximum voltage is reached when the coffee has the greatest transmittance to light which occurs at the completion of the brewing of the coffee. The richest coffee having the lowest transmittance is made with the water which first passes through the grinds in the hopper and therefore the first reading from the photodetector, when the level of coffee in the pot is the lowest level covering the photodetector, is taken as a minimum voltage output.

The circuit causes the maximum voltage as recorded in the first register to be a measure of maximum freshness and the minimum voltage as recorded in the second register to be a measure of minimum freshness or stale coffee. After the brewing of a pot of coffee is complete, the organic matters which impart flavor to the coffee gradually oxidize and the brew becomes less transparent to light. As this occurs, the voltage output of the photodetector drops from the maximum, as recorded in the first register, toward the minimum as recorded in the second register. As the voltage output falls towards the minimum, the brew is becoming stale. A LED bar graph may be employed as a display of freshness in which all ten LED's are illuminated when the coffee is "fresh" and progressively fewer LED's are illuminated as the coffee becomes progressively more "stale."

As explained in our U.S. Pat. No. 5,724,882, we have previously found that the transmittance of light through the organic compounds which impart flavor to fresh brewed coffee is at a maximum in the range between 600 nm and 1,400 nm. Fresh coffee is partially transparent to light within this range with the absorption of light directly proportional to the amount of organic matter which imparts flavor to the coffee. Degradation of the organic matter will result in decreased transmittance of light through the coffee within this wavelength range.

We have also found that the freshness of fresh brewed coffee can be extended by adding an antioxidant to the coffee grinds or to the water in the reservoir.

BRIEF DESCRIPTION OF THE DRAWINGS

A better and more complete understanding of the present invention will be had after reading of the following detailed description taken in conjunction with the following drawings wherein:

FIG. 1 is a schematic drawing of a coffee maker in accordance with the present invention;

FIG. 2 is a graph of the optical transmission of coffee after brewing;

FIG. 3 is a graph of the output voltage of the photodetector employed in the present invention as coffee is brewed in the pot and then becomes progressively more stale;

DETAILED DESCRIPTION OF THE PREFERRED EMBODIMENT

Figure 4:
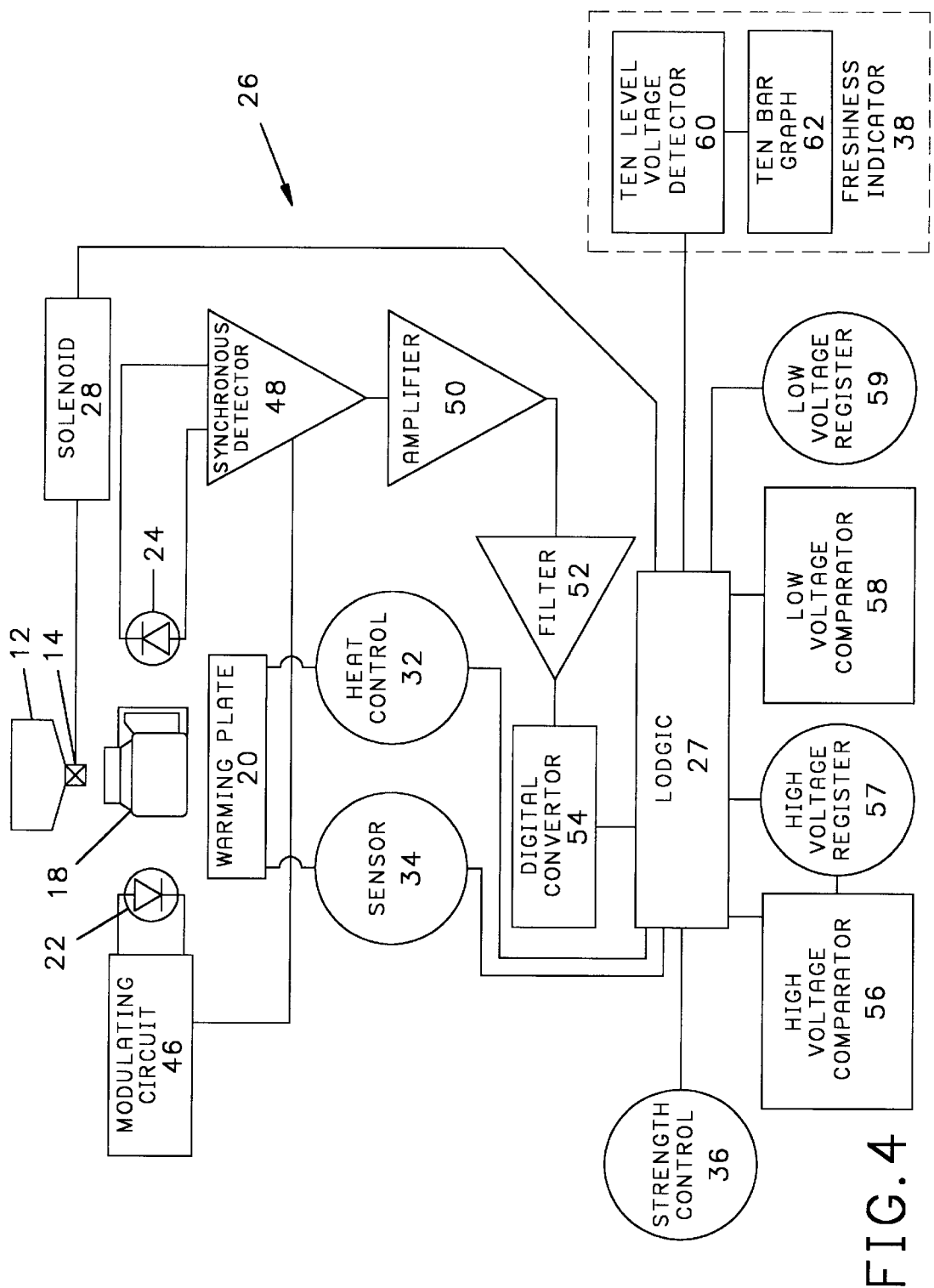
FIG. 4 is a block diagram of a circuit for use with the device of FIG. 1.

Referring to FIG. 1 the coffee maker 10 in accordance with the present invention includes a source 12 of hot water which may be a reservoir having a heater line, not shown, and an output line having a valve 14 therein for controlling the flow of hot water from the source 12. Hot water from the reservoir 12 enters a hopper 16 of the type having a porous bottom and nonporous sides for retaining coffee grinds therein and below the hopper 16 is a coffee pot 18 made of transparent material such as glass. Below the coffee pot 18 is a warming plate 20 for maintaining the coffee at a desirable temperature. Positioned at one side of the coffee pot 18 is a light source 22. The invention can employ light of any wavelength which is at least partially transmittable through coffee, but a red LED having a wavelength of 680 nm falls within the range in which coffee has a maximum transmittance to light, that being between 600 nm and 1,400 nm, and red LED's emitting a wave length of 680 nm are readily available.

Referring to FIGS. 1 and 4, on the opposite side of the coffee pot 18 is a photo detector 24 for detecting the intensity of red light from the LED 22 which passes through the liquid in the bottom of the coffee pot 18. The voltage output of the photo detector 24 is read by a circuit 26 having a logic 27 which may be a microprocessor. The circuit 26 has an output directed to a suitable control device 28, such as a solenoid, for controlling the opening and closing of the valve 14 and thereby regulating the flow of water from the source 12 through the grinds 30 in the hopper 16, and through the porous bottom of the hopper 16 and into the pot 18. In the preferred embodiment the circuit 26 includes the circuitry previously disclosed in our U.S. Pat. No. 5,724,882 whereby the valve 14 may be controlled to brew coffee to a predetermined strength.

The circuit 26 further regulates a heat control output 32 for controlling the application of power to the warming plate 20 and a heat sensor 34, which may be a thermocouple, for providing a feedback to the microprocessor 27 of the temperature of the warming plate 20. The circuit 26, therefore, can regulate the temperature at which liquid coffee in the pot 18 is maintained after it has been brewed. The device further includes a strength control 36 whereby the desired strength of the coffee to be brewed may be preset according to our prior U.S. Pat. No. 5,724,882 and the device has a freshness indicator 38 which may be a ten LED indicator or any other means which may be employed to indicate the freshness of the coffee within the pot.

We found that the transmittance of coffee deteriorates proportionately as its freshness deteriorates. FIG. 2 shows the transmittance of coffee to red light, specifically to light having a wavelength of 680 nm, over an interval of ninety minutes with the zero time corresponding to the transmittance of the fresh brewed coffee. As can be seen, the transmittance of the coffee diminishes as the coffee becomes stale.

Referring to FIG. 3 which shows a typical voltage output of a photodetector detecting the intensity of light passing through the bottom of a pot of brewed coffee as a function of time. The output of the photodetector is shown in volts on the vertical scale and time is depicted on the horizontal scale in minutes. The initial voltage reading 39 from the photodetector is very high because the brewing process began with an empty coffee pot 18 which has a higher transmittance than fresh brewed coffee. When rich coffee enters the pot 18 and interrupts the beam of light from the LED 22, the voltage output from the photodetector 24 dropped to a low point 40. As the coffee brewing process continued, the coffee grinds produced a progressively weaker coffee which gradually diluted the coffee accumulating in the pot 18, and the voltage readings from the photodetector slowly rose. In the example shown in FIG. 3, the brewing process reached its desired strength and ended after ten minutes when the voltage readout from the LED reached a peak 42. As the organic material which imparts the flavor to the coffee deteriorated over time, the transmittance of the liquid correspondingly diminished and the photodetector 24 produced a progressively lower output voltage as shown.

Eventually, the output voltage from the photodetector will drop to a level which is approximately equal to the minimum voltage reading 40 corresponding to the beginning of the brewing of the coffee. The freshness indicators 38, shown in FIGS. 1 and 4, depicts the range of the voltage outputs of the photodetector 24 from the maximum output 42 to the minimum output 40 as an indication of the freshness of the coffee through which the light from the LED 22 is being projected.

Referring to FIG. 4, we have found that it is desirable to modulate light from the LED 22 and synchronize the photodetector 24 to detect only the modulated light to thereby distinguish light from the source 22 from ambient light. The modulation of the light source 22 will thereby prevent ambient light from interfering with the accurate reading of the device. In the preferred embodiment the light may be modulated at any suitable frequency, such as 1,000 Hz. The circuit 26 therefore includes a modulating circuit 46 of the type known in the art for modulating light from the LED 22 and a synchronous detector circuit 48 such that only the light from the source 22 is being measured. The output voltage from the detector 24 is amplified by an amplifier 50, and the amplified output is thereafter filtered through a filter 52 to remove undesirable noise, after which the voltage reading is digitized by a converter 54.

The logic 27 includes a peak voltage comparator 56 and a peak voltage register 57 to find and store the peak voltage reading 42 and a minimum voltage comparator 58 and a minimum voltage register 59 to find and store the minimum voltage reading 40. Voltage readings which follow the peak reading 42 that are higher than the minimum reading 40 are directed to the freshness indicator 38, which may include a ten level voltage detector 60, the output of which is directed to a ten bar graph 62. The peak voltage 42 will cause all ten LED's to be illuminated as an indication of fresh coffee and the minimum voltage 40 will cause only one LED to be illuminated as an indication of stale coffee.

Since coffee becomes stale as a result of oxidation of the organic compounds which impart flavor, the oxidation may be reduced by reducing the temperature at which the coffee is maintained. Accordingly, the freshness of the brew may be maintained longer by employing the heat sensor 34 and heat control 32 to reduce the temperature of the warming plate 20 when the coffee has lost some predetermined degree of freshness to thereby extend the freshness of the coffee.

As stated above, the device may further include logic within the microprocessor for controlling the solenoid 28 and the valve 14 to regulate hot water entering the hopper 16 and thereby provide a brew of predetermined strength in accordance with our prior U.S. Pat. No. 5,724,882.

SECOND EMBODIMENT

Figure 5:
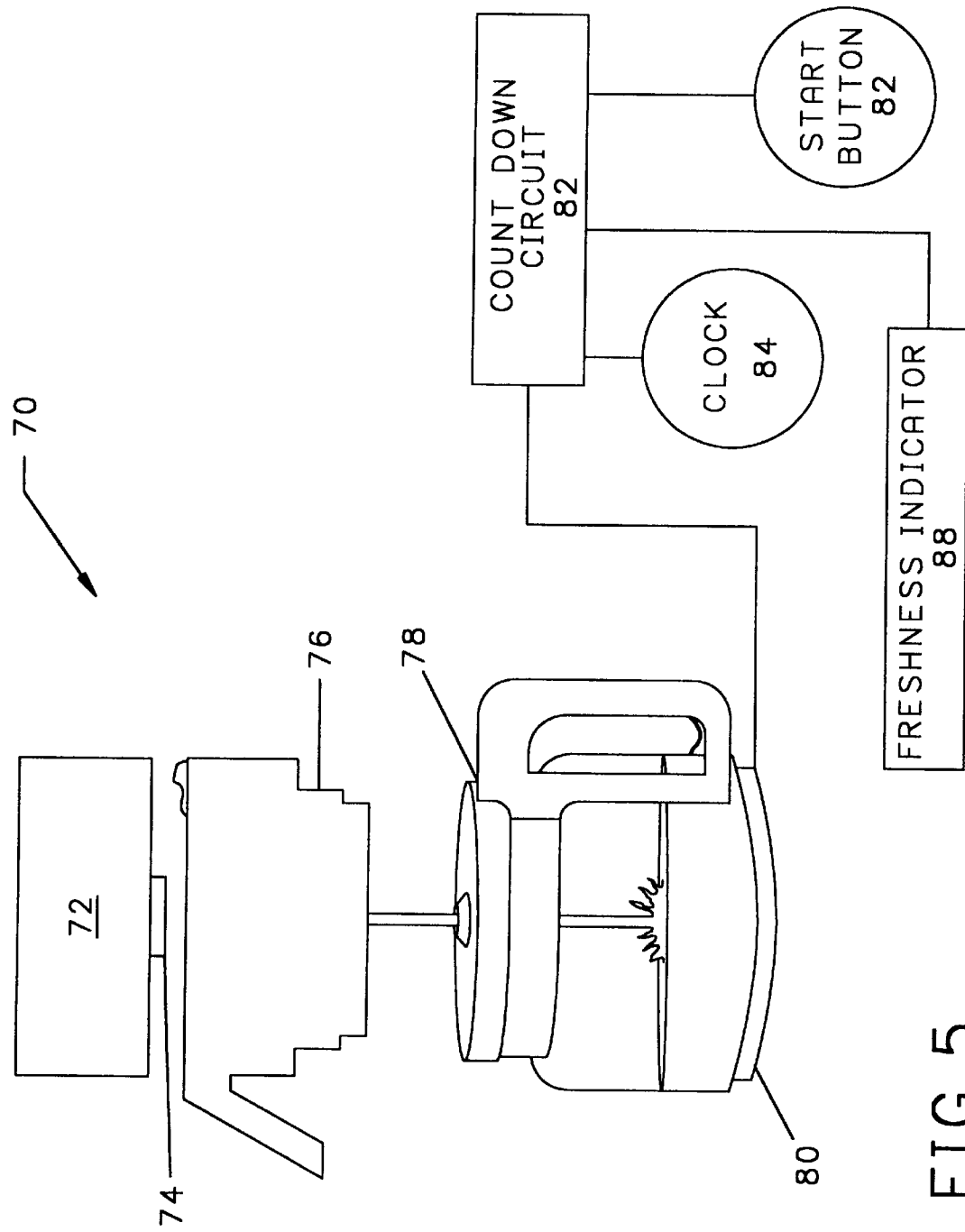
FIG. 5 is a schematic drawing of a coffee maker in accordance with a second embodiment of the invention.

The graph of the degradation of coffee freshness as shown in FIG. 3 is typical of most coffees, and a typical pot of coffee can be expected to lose its freshness over a period of 80 to 120 minutes as shown. A simplified embodiment of the invention could, therefore, be constructed as shown in FIG. 5.

In this embodiment a coffee maker 70 includes a reservoir 72, a valve 74, a hopper 76, a pot 78 and a heating element 80, all in accordance with the prior art. After the reservoir 72 has been filled with water and the hopper 76 filled with coffee grinds the brewing process is commenced by some appropriate means, such as pressing a start button 82.

The device includes a clock 84 for measuring time from the commencement of the brewing process and a freshness display, which may be a ten LED bar indicator 88 in which all the LED's are illuminated to indicate fresh coffee and one LED is illuminated to indicate stale coffee. A count down circuit 90 allows a fixed interval of time for the brewing of the process to occur, then the circuit 90 illuminates all ten LED's 88 as an indicate that the coffee is brewed and is fresh. The circuit 90 then turns off the LED's 88 one at a time with a fixed interval of time, such as ten minutes, between each turn off. After an interval of time, between 80 and 120 minutes, the circuit 90 will have turned off nine of the LED's so that the indicator 88 will show the coffee as being stale.

It should be apparent that the freshness indicator 90 provides only an estimate of the freshness of the coffee and not a measure of coffee freshness as is provided by the first embodiment.

THIRD EMBODIMENT

We have also determined that the freshness of coffee may be further extended by the provision of an anti-oxidant to thereby reduce the oxidation of the organic matter which imparts flavor to the coffee. Any of a number of anti-oxidants may be used, and Vitamin C (ascorbic acid) is a suitable anti-oxidant which is readily available. Vitamin C in powdered or tablet form may therefore be added to the grinds in the hopper 16 or to the water in the reservoir 12 such that they are absorbed by the water from the source 12 and enter the coffeepot 18 to extend the freshness of the coffee brewed therein.

As can be seen from the graph of the transmittance of coffee shown in FIG. 3, the rate at which the transmittance of the coffee diminished fits a simple exponential decay and can be expressed mathematically as:

$$I = I_o \exp(-t/t_{1/e})$$

Where I. Is the initial photo voltage and $t_{1/e}$ is the time for the photo voltage to decay to 0.3679 of its initial value.

When Vitamin C is added to the grinds or the water from which a pot of coffee is brewed, the time constant for the decay is extended.

EXAMPLES

French Roast coffee beans were ground for 10 seconds and used to make three typical six cup pots of coffee. No vitamin C was added to the first pot, 250 mg of Vitamin C was added to the grinds to make the coffee in the second pot, and 500 mg of vitamin C was added to the grinds to make the coffee in the third pot. The time constants for the decay of the transmittance were then measured and are shown below:

| Fresh Roast Ground Coffee Sample | | |
|---|---|---|
| Pot Number | Vitamin C (mg) | Decay Time $t_{1/e}$ in minutes |
| 1 | 0 | 42 |
| 2 | 250 | 104 |
| 3 | 500 | 175 |

Referring again to FIG. 1, according to the third embodiment of the invention the coffee maker 10 of the first embodiment is provided with an antioxidant dispenser 94. The dispenser 94 is actuated by the circuit 26 to dispense a predetermined dosage of an antioxidant, such as one or two 250 mg tables of Vitamin C into the hopper 16 as shown at the commencement of the brewing cycle. Alternately, the dispenser 18 could be adapted to dispense an antioxidant into the water in either the reservoir 12 or the pot 18. The freshness indicator 38 will then display the freshness of the coffee in the pot 18 and will show an extended decay time consistent with the examples above.

It should be appreciated that the antioxidant dispensed by the dispenser 94 will change the rate of degradation of the coffee. The simple clock 84 of the second embodiment cannot be used to provide a reasonable estimate of the rate of degradation of coffee to which an antioxidant has been added as described with respect to the third embodiment.

Although several embodiments of the invention have been depicted, many modifications and variations can be made without departing from the true spirit and scope of the invention. It is therefore the intent of the following claims to cover all such modifications and variations that come within the true spirit and scope of the invention.

What is claimed:

1. A device for monitoring the freshness of coffee comprising
   a container for containing coffee therein,
   a light source for providing a beam of light having a wavelength which is at least partially transmissible through coffee,
   said light source positioned to direct said beam of light through coffee in said container,
   a photodetector means for converting light energy into an electric potential for detecting the intensity of light from said light source,
   said photodetector means positioned to receive light from said light source after passing through coffee in said container,
   means for determining a peak voltage from said photo detector means,
   a display means for displaying freshness wherein said peak voltage is displayed as fresh and a lesser voltage from said photodetector means is displayed as less fresh.

2. A device in accordance with claim 1 and further comprising:
   modulating means for modulating light from said light source, and synchronous means connected to said photodetector means for detecting only light from said modulated light source.

3. A device in accordance with claim 1 wherein said light source is a red LED.

4. A device in accordance with claim 1 wherein said light has a wavelength between 600 nm and 1,400 nm.

5. A device in accordance to claim 1 wherein said container is transparent and said beam of light is directed thought said container.

6. A device in accordance with claim 1 wherein said light source has a wavelength of about 680 nm.

7. A device in accordance with claim 1 and further comprising, means for heating said container, means for sensing the temperature of said container, control means responsive to said means for heating, said means for sensing, and said photo detector means for lowering the temperature of said coffee in said container when said photo detector means detects a given drop in voltage output below said peak voltage whereby the freshness of said coffee in said container can be extended after it reaches a given reading of freshness.

8. The method of monitoring the freshness of liquid coffee comprising the steps of:

providing a container, retaining said coffee in said container, providing a source of light having a wave length which is a least partially transmissible through coffee, directing light from said source of light through said coffee while said coffee is in said container, providing a detector means for detecting light from said source of light and for producing an electric potential in response to said detected light, positioning said detector means to receive light from said source of light after it has passed through said coffee, providing means for measuring said potential produced by said detector means, determining a peak electric potential from said means of measuring, and providing a display for displaying a measurement of freshness wherein said peak electric potential is displayed as being fresh and a potential which is less than said peak electric potential is displayed as being less fresh.

9. The method of claim 8 and further comprising the steps of modulating light emanating from said course of light and providing means for detecting only said modulated light from said light source.

10. A coffee maker comprising a source of hot water, a hopper below said source of hot water, said hopper for retaining coffee grinds, a transparent pot below said hopper, said pot having a lower portion, a light source for generating a beam of light having a wave length which is at least partially transmissible through coffee, said beam of light directed through said lower portion of said pot, a photodetector positioned to receive said beam of light after it passes through said pot, said photodetector generating a voltage, means for determining a peak voltage from said photodetector, and display means for displaying freshness wherein said peak voltage is displayed as fresh and lesser voltages are displayed as less fresh.

11. The coffee maker of claim 10 and further comprising a heater for heating said pot while said pot is under said hopper.

12. The coffee maker of claim 10 and further comprising a dispenser for dispensing an antioxidant into one of said source of hot water, said hopper, and said pot.

13. The coffee maker of claim 11 and further comprising means for sensing the temperature of said pot, and logic means responsive to said means for sensing and to said heater for controlling the temperature of said pot whereby said logic means causes said temperature of said pot to drop after said voltage from said photodetector drops below a given level.

* * * * *

UNITED STATES PATENT AND TRADEMARK OFFICE
CERTIFICATE OF CORRECTION

PATENT NO. : 5,956,151
DATED : September 21, 1999
INVENTOR(S) : Zajac et al.

It is certified that error appears in the above-indentified patent and that said Letters Patent is hereby corrected as shown below:

In column 5, line 59, after "Where I." delete ".Is" and substitute --is--.

In column 7, line 28, beginning of the line, delete "a" and substitute --at--.

Signed and Sealed this

Twenty-fifth Day of April, 2000

Attest:

Q. TODD DICKINSON

Attesting Officer

Director of Patents and Trademarks